United States Patent [19]

Stuart

[11] Patent Number: 5,617,212
[45] Date of Patent: Apr. 1, 1997

[54] OPEN-PATH GAS MONITORING

[75] Inventor: Derek Stuart, Sheppfield, United Kingdom

[73] Assignee: Land Instruments International Limited, Dronfield, England

[21] Appl. No.: 407,572

[22] Filed: Mar. 20, 1995

[30] Foreign Application Priority Data

Mar. 19, 1994 [GB] United Kingdom ............... 9405434

[51] Int. Cl.$^6$ ................................................ G01N 21/61
[52] U.S. Cl. ........................................ 356/438; 356/435
[58] Field of Search ............................ 356/433, 434, 356/435, 437, 438, 439; 250/573, 575

[56] References Cited

U.S. PATENT DOCUMENTS

| | | | |
|---|---|---|---|
| 3,510,666 | 5/1970 | Topol | 250/574 |
| 4,537,510 | 8/1985 | Takahasi | 356/435 |
| 5,028,790 | 7/1991 | McGowan et al. | 356/438 |
| 5,077,480 | 12/1991 | Traina . | |

FOREIGN PATENT DOCUMENTS 1223453  4/1968  United Kingdom .

*Primary Examiner*—Richard A. Rosenberger
*Attorney, Agent, or Firm*—Caesar, Rivise, Bernstein, Cohen & Pokotilow, Ltd.

[57] ABSTRACT

The invention relates to apparatus for open-path gas monitoring and is particularly concerned with measuring the opacity of stack gases. Single and double pass systems to provide an optical across the stack, are known, but to provide meaningful data, gain compensation is required to deal with temperature variations and the possibility of ageing of electronic components. The object of the present invention is to provide an instrument that meets the above requirement but without moving components, which objective is met by a construction comprising a transceiver unit adapted to be mounted on one side of the optical path; a passive reflector adapted to be mounted on the other side of the path; and electronic control circuitry, the transceiver unit comprising:

(i) first and second light detectors;
(ii) first light source capable of projecting a beam of light along the optical path
(iii) second light source capable of flooding the first and second detectors with light; and
(iv) means to alternate activation of the first and second light sources at a predetermined frequency.

5 Claims, 2 Drawing Sheets

OPEN-PATH GAS MONITORING

FIELD OF THE INVENTION

This invention relates to apparatus for open-path gas monitoring, particularly for the measurement of smoke and dust content of stack gases, but also applicable for the measurement of particulates and gaseous species in the atmosphere.

BACKGROUND OF INVENTION

Currently, the standard method used is optical transmissometry, and the quantity measured is opacity (Op), defined as the fraction of incident light which is lost in transmission through an optical medium.

In principle, all that is needed is a light source mounted on one end of the optical path and a detector mounted at the other. In practice, a more sophisticated arrangement is needed to compensate for variations in source intensity, detector response, etc. which would otherwise appear as changes in the opacity measurement.

A preferred form of opacity measurement system known in the prior art is illustrated in FIG. 1 of the drawings hereto, which shows a double-pass system, with a transceiver mounted on one side of the path and a passive reflector on the other side. This has the advantage that it permits an automatic calibration check to be performed by means of a reflector intermittently placed in front of the transceiver.

To provide meaningful data, gain compensation is required to deal with the temperature variations and ageing electronic components, and two prior art methods for measuring opacity with gain compensation are known. Both rely on continuously moving reflectors. The first method is used in the Erwin Sick RM41 instrument. This has a single detector which alternately views the distant retroreflector and internal, partially reflecting chopper. This does away with the need for the second detector and permits an external zero reflector to be used to check the instrument calibration. The method works well provided high quality (i.e. expensive) bearings are used for the chopper motor. The second method, employed in the United Sciences Model 500 instrument, combines the zero reflector with the partially reflecting chopper, thereby simplifying the instrument, but only at the cost of losing the independent zero check. This method still suffers from the drawback that it requires a continuously rotating reflector.

OBJECTS OF THE INVENTION

A basic object of the invention is to provide an improved, reliable and accurate instrument for open-path monitoring of gases and in particular for measurement of the density of smoke emissions from industrial chimneys and flues.

SUMMARY OF THE INVENTION

According to the present invention there is provided an instrument for monitoring gases, comprising a transceiver unit adapted to be mounted on one side of the optical path; a passive reflector adapted to be mounted on the other side of the path; and electronic control circuitry, the transceiver unit comprising:

(i) first and second light detectors;
(ii) first light source capable of projecting a beam of light along the optical path
(iii) second light source capable of flooding the first and second detectors with light; and
(iv) means to alternate activation of the first and Hertz light sources at a frequency of say 1 Hertz.

DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF THE PREFERRED EMBODIMENT

Figure 1:
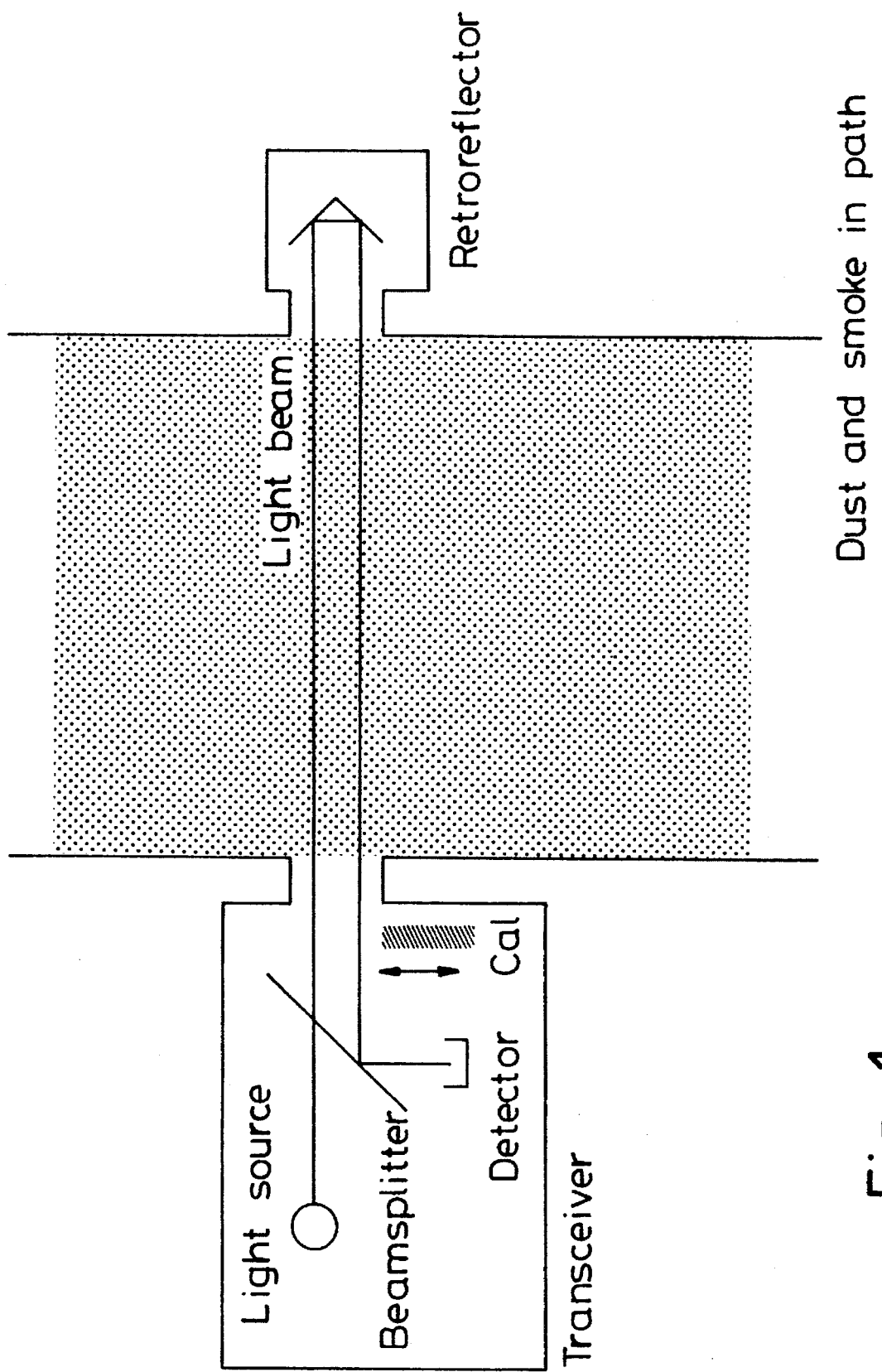
FIG. 1 is depiction of a prior art opacity measurement system.
Figure 2:
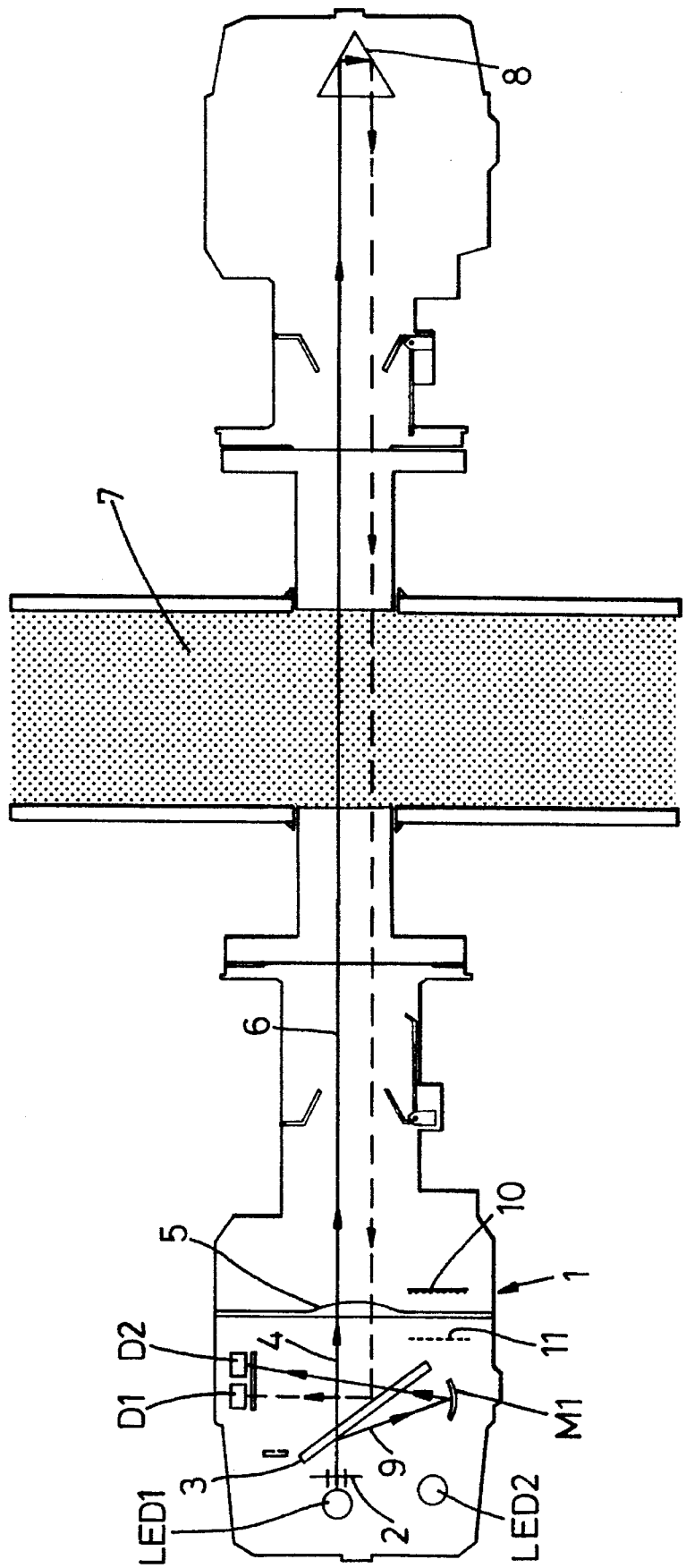
FIG. 2 is an operational diagram of the present invention.

One embodiment of the invention will now be described with reference to FIG. 2 of the drawings which is a schematic sectional side elevation of an open-path gas monitoring system in accordance with the invention. The exposed optical surfaces of both the transceiver and reflector are protected by air purges.

In transceiver 1, light from a first source LED 1 passes through a diffuser 2 and on to a 50/50 beamsplitter 3. The transmitted portion 4 of light passes on to a lens 5 which projects a well defined, collimated beam 6 across the measuring path 7 to distant reflector 8. Light returned from the retroreflector 8 is focused by the lens 5 onto a first detector D1. The other portion 9 of light originally reflected by the beamsplitter 3 falls on concave mirror M1 which focuses it onto a second detector D2. The opacity value Op can be calculated from the signals $S_1$ and $S_2$ measured by D1 and D2 respectively, scaled by a calibration factor, C.

$$Op = 1 - \frac{S_1}{S_2} C$$

Principal advantages of the instrument in accordance with the invention over previous methods are that it works continuously (with response time of less than 1 second) and that it requires no moving parts. Gain compensation is achieved by using a second light source LED 2 to flood both the first and second detectors D1 and D2 with light. Because no focusing optics are used there is no possibility of misalignment and so any relative change in sensitivity between the first and second detectors D1 and D2 will lead to a difference in the ratio of signals from the second light source LED 2. By alternating the first and second light sources LED 1 and LED 2 approximately once every second, it is possible to compensate for any relative gain change between the first and second detectors D1 and D2. Thus the measured opacity is:

$$Op = 1 - \frac{S_1}{S_2} CG$$

where $G = \frac{S_2}{S_1}$ when $LED2$ is illuminated

Preferably, a motorised reflector 10 is mounted in front of the lens 5 and an attenuator grid 11 is mounted behind the lens, thereby permitting an intermittent zero and upscale calibration checking. The zero reflector 10 has the additional benefit that it can measure and correct for any contamination of the lens 5.

In conclusion, the instrument in accordance with the invention offers an accurate, stable method for measuring the opacity of gases in an open path with no continuously moving parts. The only moving parts are used for intermittent calibration checks. Very high stability is achievable by using the second light source LED 2 to compensate for changes in responsivity and gain between the two detectors D1 and D2.

I claim:

1. An instrument for monitoring gases passing through a stack and comprising a transceiver unit adapted to be mounted on one side of the stack; a passive reflector adapted to be mounted on the other side of the stack; and electronic control circuitry, said transceiver unit comprising:

(i) first and second light detectors;

(ii) a first light source adapted for projecting a beam of light along an optical path;

(iii) means for splitting said beam of light, thereby forming a portion of said beam of light, and directing said portion of said beam of light to said second light detector;

(iv) a second light source adapted for flooding said first and second detectors with a second light, said second light not passing through the gases;

(v) means to automatically alternate activation of said first and second light sources at a predetermined frequency so that any light detected by said first and second detectors at any instant originates from either said first light source or said second light source, but not both, said automatic alternate activation removing D.C. offsets and correcting for short term differential gain changes between said first and second light detectors.

2. An instrument for monitoring gases as in claim 1, wherein the alternate activation of the first and second light sources is at a frequency of 1 Hertz.

3. An instrument for monitoring gases as in claim 1 or claim 2, wherein the exposed optical surfaces of both the transceiver and reflector are protected by air purges.

4. An instrument for monitoring gases as in any one of claims 1 to 3, wherein a reflector is mounted in front of the lens and an attenuator grid is mounted behind the lens, there being means to introduce the reflector and the attenuator grid into the optical path thereby permitting an intermittent zero to be created to enable upscale calibration of the instrument.

5. An instrument for monitoring gases as in claim 4, wherein motor drive means is provided for the intermittent introduction of the reflector and attenuator grid into the optical path.

* * * * *